US00PP12899P2

(12) United States Plant Patent

Mowrey et al.

(10) Patent No.: US PP12,899 P2

(45) Date of Patent: Sep. 3, 2002

(54) STRAWBERRY PLANT NAMED 'SAN JUAN'

(75) Inventors: Bruce D. Mowrey, Watsonville; Larry T. Kodama, Freedom; JoAnne F. Coss, Salinas; Joseph I. Espejo, Jr., Watsonville; Thomas M. Sjulin, Aromas, all of CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/524,581

(22) Filed: Mar. 13, 2000

(51) Int. Cl.[7] ..... A01H 5/00

(52) U.S. Cl. ..... Plt./209

(58) Field of Search ..... Plt./209, 208

(56) References Cited

U.S. PATENT DOCUMENTS

PP8,086 P * 1/1993 Nelson et al. ..... Plt./209

* cited by examiner

*Primary Examiner*—Bruce R. Campell

*Assistant Examiner*—Susan B. McCormick

(74) *Attorney, Agent, or Firm*—Pennie & Edmonds LLP

(57) ABSTRACT

This invention relates to a new and distinct variety of strawberry named 'San Juan'. The variety is similar to the varieties 'Commander' and 'Lido'. The variety is distinguished from 'Commander' and 'Lido', in particular, by its globose to flat globose habit, medium to strong interveinal blistering, weak to medium weak leaf glossiness, medium dense stipule pubescence, larger calyx diameter relative to the corolla, conical to almost cylindrical fruit, moderate differences in shapes of primary and secondary fruits, narrow band without achenes, and fruit with firm flesh and medium acidity.

6 Drawing Sheets

BACKGROUND OF THE INVENTION

The new variety originated as a result of a controlled cross between the strawberry plants 'Lido' (U.S. Plant Pat. No. 10,534) and '33×257' (unpatented variety) in an ongoing breeding program, and was discovered as a seedling in a controlled breeding plot at Monterey County, Calif. in May, 1996. The original seedling of the new cultivar was asexually propagated by stolons at McArthur, Shasta County, Calif. Propagules were transplanted to a controlled breeding plot in Monterey County, Calif., where the variety was identified and selected for further evaluation. 'San Juan' was subsequently asexually propagated and underwent further testing in the Monterey Bay area, California for three years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'San Juan'. The variety is botanically identified as *Fragaria×ananassa*. The new variety is distinguished from other varieties by a number of characteristics as set forth in Tables 1–6.

The varieties which we believe to be similar to 'San Juan' from those known to us are 'Commander' (U.S. Plant Pat. No. 7,024) and 'Lido' (U.S. Plant Pat. No. 10,534). There are several characteristics of the new variety that are different from, or not possessed by 'Commander' and 'Lido'. The new variety has a globose to flat globose habit, medium to strong interveinal blistering, weak to medium weak leaf glossiness, medium dense stipule pubescence, a larger calyx diameter relative to the corolla, conical to almost cylindrical fruit, moderate differences in shapes of primary and secondary fruits, a narrow band without achenes, and fruit with firm flesh and medium acidity. Plants of 33×257 were lighter green and more vigorous than those of 'San Juan'. Fruit size and flavor were inferior to the 'San Juan' variety.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
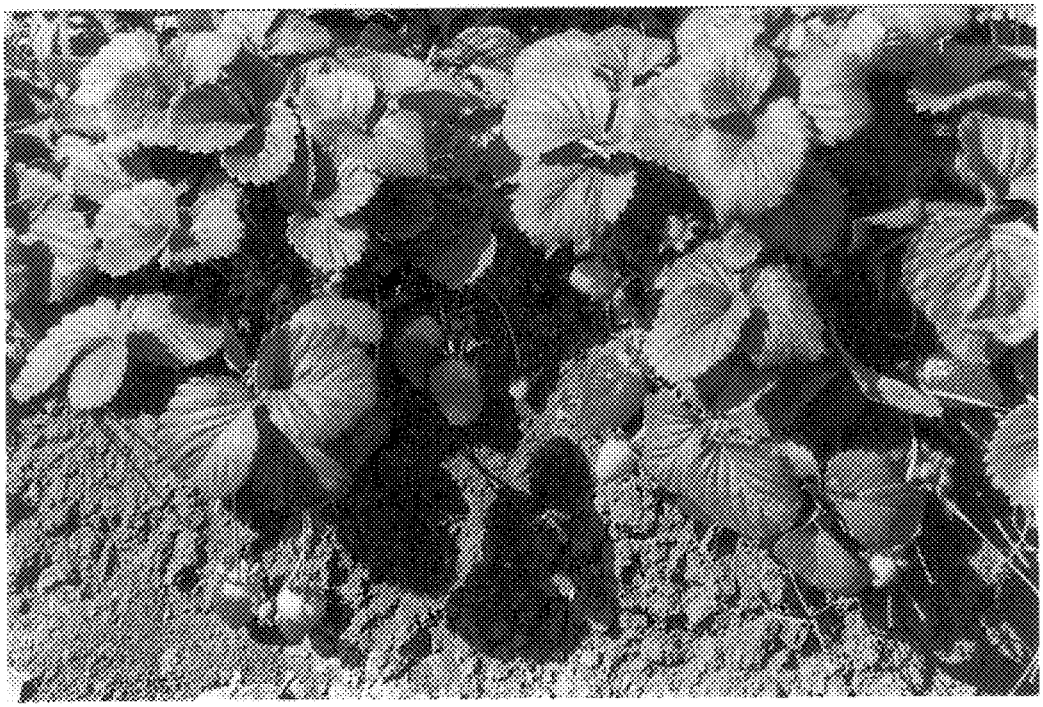
FIG. 1 shows a close-up photo of the whole plant.
Figure 2:
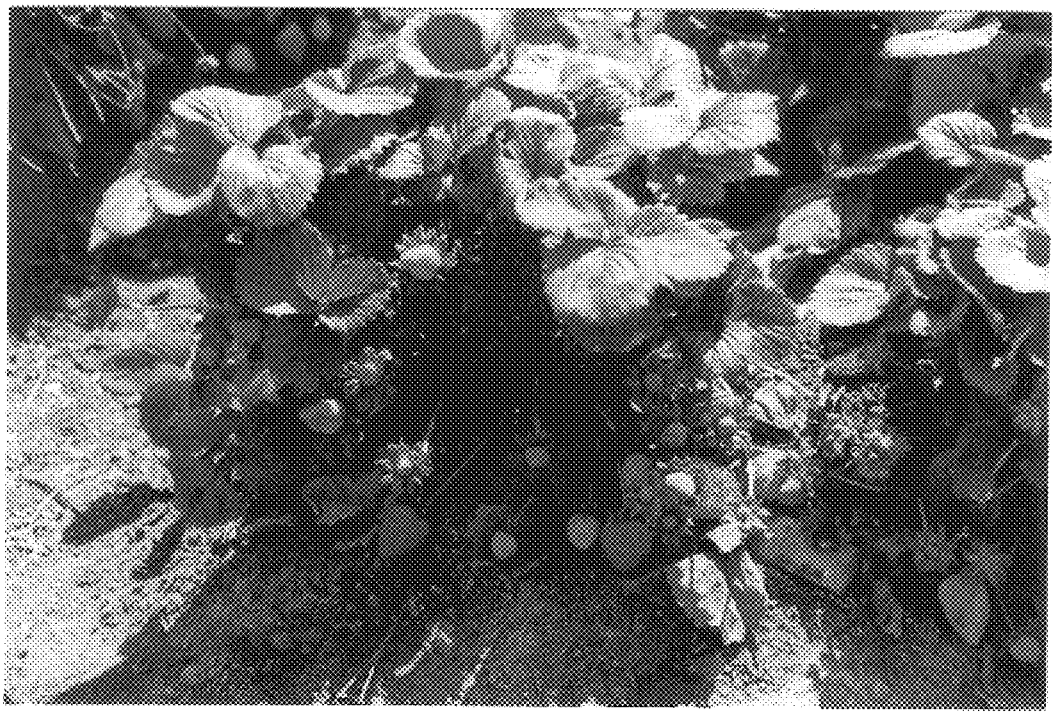
FIG. 2 shows the whole plant.
Figure 3:
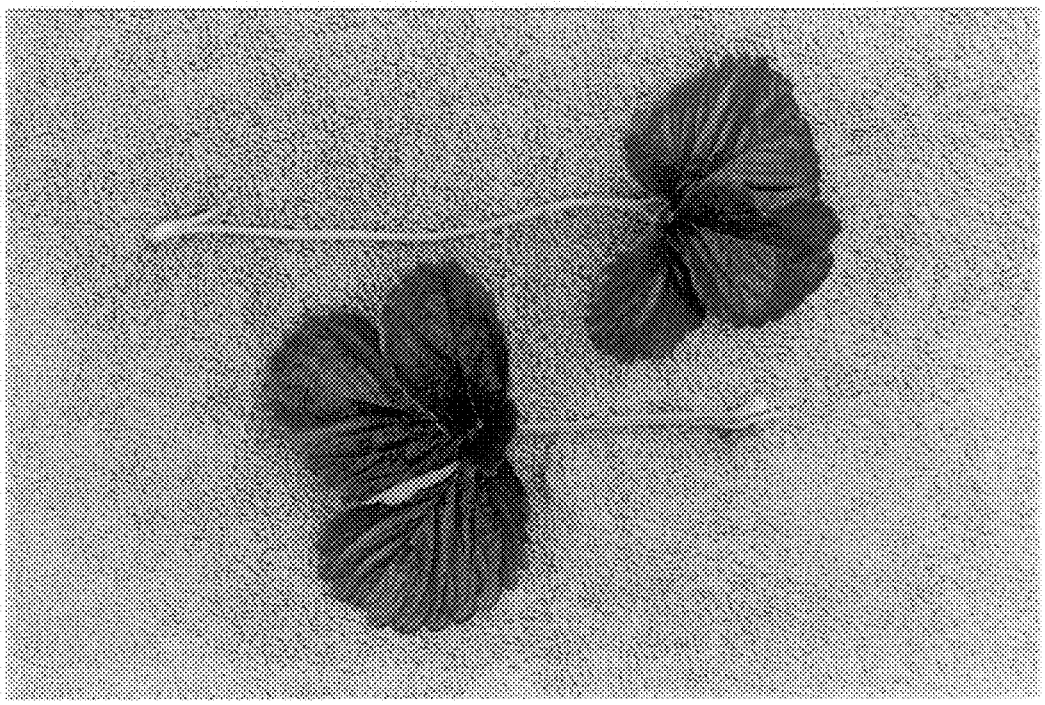
FIG. 3 shows the leaves of the plant.
Figure 4:
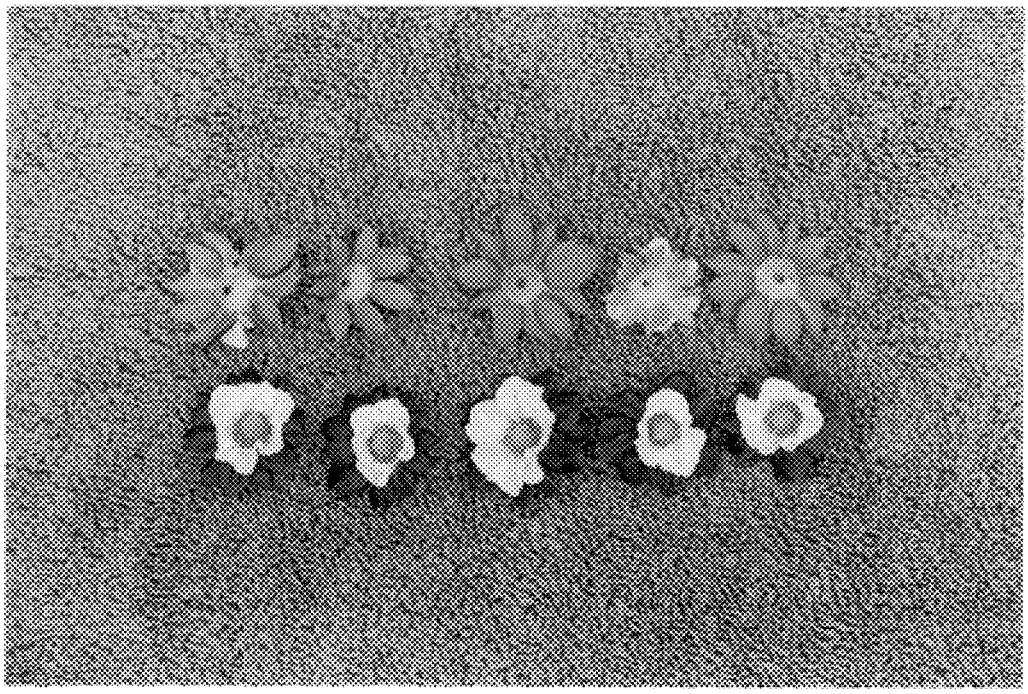
FIG. 4 shows the upper side and the under side of the flowers.
Figure 5:
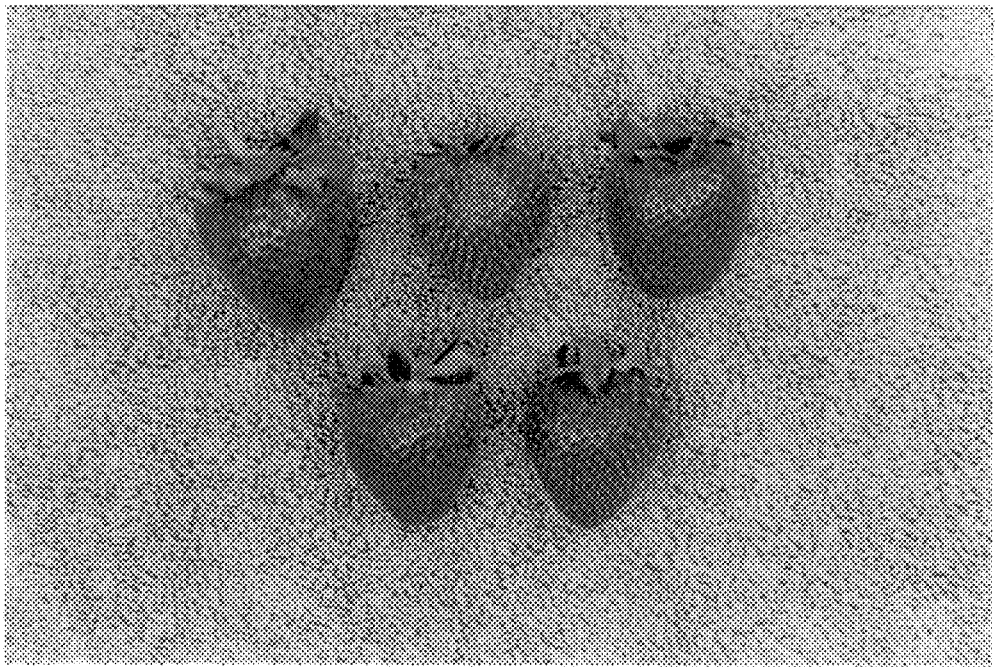
FIG. 5 shows a close-up of the fruit.
Figure 6:
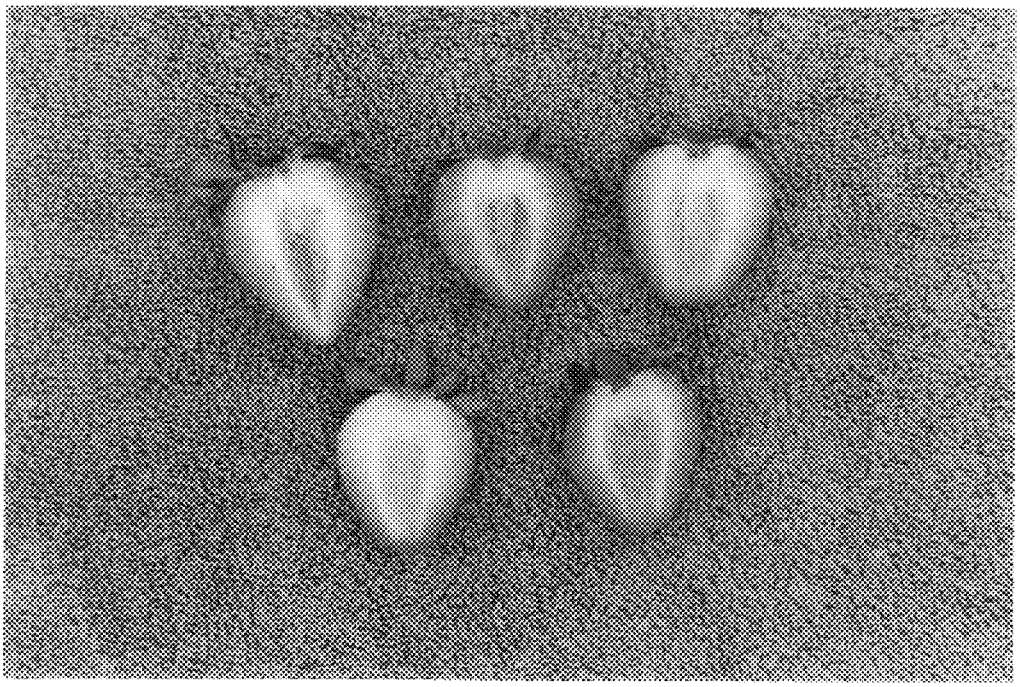
FIG. 6 shows the fruit in longitudinal cross-section.

The following detailed description of the new variety is based upon observations taken of plants and fruit grown in Monterey County, Calif., U.S.A. Observations of 'San Juan', 'Commander' and 'Lido' were taken in side by side comparison in 1999. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2 and 3. In the tables, the flowers described are secondary flowers except where indicated. The petal color of 'San Juan' is white, 155C in the R.H.S. Colour Chart. The fruit described is the secondary fruit on one year old plants. Fruit and flower measurements are an average of both primary and secondary fruit and flowers.

Table 1 provides information on the plant and fruit characteristics of the new variety 'San Juan' compared with characteristics of 'Commander' and 'Lido'. Table 2 provides additional information of the plant and fruit characteristics of the new variety 'San Juan' compared with characteristics of the varieties 'Commander' and 'Lido'. Table 3 provides reactions of the new variety to stresses as compared to the varieties 'Commander' and 'Lido'. Tables 4 and 5 provide information of the new variety's reaction to pests and diseases, respectively, compared to the varieties 'Commander' and 'Lido'. Table 6 provides isozyme characteristics of the new variety as compared to the varieties 'Commander' and 'Lido'.

The leaf margin is crenate. The leaf texture is blistered and the leaf shape is rounded. The mid vein color on the terminal leaflet is RHS 151B. Leaf venation is pinate.

The average petiole diameter is 0.4 cm. The average length of the petiole on the terminal leaflet is 1.3 cm.

Petal shape is ovate to rounded. The petal margin is entire. The petal texture is smooth to slightly crinkled. The shape of the petal apex is rounded and the petal base is obtuse. The average number of petals per flower is 6.4.

The average length of the sepal is 1.17 cm. The average width of the sepal is 0.63 cm. The average number of sepals is 12.7. The color of the upper side of the sepal is dark green (138A) and the color of the lower side of the sepal is medium green (138B).

The achene color is green-yellow to grayed red (150B to 180A). The average number of achenes per berry is 359.

The average number of stolons per plant is 16. Stolons are tapered with an average diameter of 3 mm near the point of origination (at the mother plant), which average diameter gradually increases to 5 mm near the point of termination (at the daughter plant).

The anthocyanin pigmentation of various plant organs is red to purple in color.

The texture of the flesh is firm melting.

The initial bloom on the 'San Juan' variety occurs in early-March to mid-April in the vicinity of Watsonville, Calif. and continues until late fall.

TABLE 1

DETAILED COMPARISON of 'SAN JUAN', 'COMMANDER', AND 'LIDO'

| | San Juan | Commander | Lido |
|---|---|---|---|
| Plant Characteristics | | | |
| Height of Plant (cm) | 28.0 | 24.1 | 26.4 |
| Spread of Plant (cm) | 47.1 | 46.8 | 43.9 |
| Number of Crowns | 4.6 | 3.9 | 2.6 |
| Leaf Characteristics | | | |
| Terminal Leaflet Width (cm) | 7.6 | 7.1 | 7.9 |
| Terminal Leaflet Length (cm) | 8.0 | 7.7 | 7.4 |
| Terminal Leaflet Length/Width Ratio | 1.05 | 1.09 | 0.93 |
| Number of Teeth/Terminal Leaflet | 22.3 | 17.2 | 20.2 |
| Color of upper side of leaf | Medium to dark green 147A | Medium green 147A | Medium to dark green 147A |
| Color of under side of leaf | Light green 147C | Light green 147C | Light green 147C |
| Petiole Length (cm) | 23.8 | 22.1 | 19.4 |
| Petiole color | yellow green 149A | yellow green 149A | yellow green 149A |
| Bract Frequency | 58% Single or paired | 17% Single only | 58% Single or paired, typically single |
| Stipule Length (cm) | 3.4 | 3.2 | 2.9 |
| Stipule Width (cm) | 1.0 | 0.9 | 0.9 |
| Flower Characteristics | | | |
| Petal Width (cm) | 1.42 | 1.34 | 1.28 |
| Petal Length (cm) | 1.30 | 1.27 | 1.08 |
| Petal Length/Width Ratio | 0.92 | 0.94 | 0.84 |
| Flower Diameter (cm) | 3.3 | 3.2 | 2.8 |
| Calyx Diameter (cm) | 3.9 | 3.9 | 3.1 |
| Fruit Characteristics | | | |
| Fruit Width (cm) | 4.1 | 4.5 | 4.8 |
| Fruit Length (cm) | 4.6 | 4.7 | 4.3 |
| Fruit Length/Width Ratio | 1.13 | 1.04 | 0.91 |
| Average Berry Size (g) | 27.5 | 24.5 | 23.8 |
| Fruit Skin Color | Dark Red 53B | Orange red 45A | Orange Red 46A |
| Fruit Flesh Color | Red 44A and white 155A | Light red to orange red 41A & white | Pale rose 41B & white |
| Total Yield (g/plant) | 1,212 | 1,399 | 671 |

TABLE 2

CHARACTERISTICS OF 'SAN JUAN', 'COMMANDER', AND 'LIDO'

| | San Juan | Commander | Lido |
|---|---|---|---|
| Plant | | | |
| Habit | globose to flat globose | flat globose | globose |
| Density | medium | medium | open |
| Vigor | medium | medium | weak |

TABLE 2-continued

CHARACTERISTICS OF 'SAN JUAN', 'COMMANDER', AND 'LIDO'

| | San Juan | Commander | Lido |
|---|---|---|---|
| Leaf | | | |
| Shape in cross section | flat to slightly convex | slightly concave | concave |
| Interveinal blistering | medium to strong | weak | medium |
| Glossiness | weak to medium weak | weak | medium weak |
| Number of leaflets | sometimes more than 3 (approx. 17% of leaves) | 3 only | 3 only |
| Terminal leaflet margin profile | revolute to flat | flat | flat |
| Terminal leaflet shape of base | obtuse to rounded | rounded | obtuse |
| Terminal leaflet shape of teeth | rounded | obtuse | rounded |
| Stipule pubescence | medium dense | medium | sparse to medium |
| Petiole pubescence | medium | medium | sparse to medium |
| Petiole pose of hairs | outward to downward | outward | outward to upward |
| Stolon | | | |
| Number | 16 | — | — |
| Anthocyanin coloration | strong | — | — |
| Thickness | 3–5 mm | — | — |
| Pubescence | medium | — | — |
| Inflorescence | | | |
| Position relative to foliage | beneath to level with | level with to above | level with to above |
| Diameter of calyx relative to corolla | larger | same size to larger | same size |
| Diameter of inner calyx relative to outer | same size | same size | larger |
| Spacing of petals | overlapping | overlapping | overlapping |
| Fruiting Truss | | | |
| Attitude at first picking | prostrate | prostrate | erect to semi-erect |
| Length | medium | medium | short to medium |
| Fruit | | | |
| Predominant shape | conical to almost cylindrical | conical to bi-conical | cordate |
| Difference in shapes between primary and secondary fruits | moderate | slight | moderate to marked |
| Band without achenes | narrow | narrow to medium | very narrow |
| Unevenness of surface | medium | weak | medium |
| Evenness of color | even | slightly uneven | even |
| Glossiness | very strong | strong | very strong |
| Insertion of achenes | level with surface | level with surface | below to level with surface |
| Insertion of calyx | level | level | in a basin |
| Pose of the calyx segments | spreading to reflexed | spreading | spreading to reflexed |
| Size of calyx in relation to fruit | same size | same size | smaller |
| Adherence of calyx | strong | strong | strong |
| Firmness of flesh | firm | medium | medium firm |
| Evenness of flesh color | slightly uneven to even | slightly uneven | slightly uneven |
| Distribution of flesh color | marginal and central | marginal and central | only marginal to marginal and central |
| Hollow center size | medium | medium | absent |
| Sweetness | medium to strong | medium to strong | strong |
| Texture when tasted | medium | medium | medium |
| Acidity | medium | weak to medium | weak |
| Time of Flowering | medium to late | early to medium | early to medium |
| Harvest Interval | week ending May 1, 1999 to week ending October 30, 1999 | week ending April 17, 1999 to week ending October 30, 1999 | week ending April 24, 1999 to week ending October 30, 1999 |
| Time of Bearing | partially everbearing | partially everbearing | partially everbearing |

REACTION TO STRESS

TABLE 3

| | San Juan | Commander | Lido |
|---|---|---|---|
| Reaction to Stress | | | |
| high pH | Moderately Resistant | Moderately Resistant | Moderately Resistant |
| high soil salt levels | Moderately Resistant | Moderately Resistant | Moderately Resistant |

PEST AND DISEASE RESISTANCE AND SUSCEPTIBILITY

TABLE 4

| | San Juan | Commander | Lido |
|---|---|---|---|
| Reaction to Pests | | | |
| *Tetranychus urticae* | moderately susceptible | moderately susceptible | susceptible |
| *Aphis* spp. | susceptible | susceptible | susceptible |
| *Lygus hesperus* | susceptible | susceptible | susceptible |

TABLE 5

| | 'San Juan' | 'Commander' | 'Lido' |
|---|---|---|---|
| Reaction to Diseases | | | |
| Botrytis fruit rot | susceptible | susceptible | moderately resistant |
| Powdery mildew | moderately susceptible | — | — |
| Verticillium wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

ISOZYME ANALYSIS

In addition to the morphological description above, the new cultivar 'San Juan' has been analyzed to obtain an indication of its genetic makeup to provide further means for identifying the new variety and distinguishing it from some other somewhat similar and/or related strawberry varieties. Specifically, leaf samples of 'San Juan', 'Commander', and 'Lido' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the three varieties is presented in Table 4, with the letters representing the banding patterns for each enzyme as designated in the above-identified article.

TABLE 6

ISOZYME ANALYSIS FOR 'SAN JUAN', 'COMMANDER', AND 'LIDO'

| Locus | San Juan | Commander | Lido |
|---|---|---|---|
| PGI | A2 | A4 | A3 |
| LAP | B3 | B3 | B3 |
| PGM | C4 | C4 | C2 |

What is claimed is:

1. A new and distinct variety of strawberry plant, substantially as shown and described.

* * * * *